US011179453B2

(12) United States Patent
Kumar et al.

(10) Patent No.: US 11,179,453 B2
(45) Date of Patent: Nov. 23, 2021

(54) IMMUNOGENIC COMPOSITION HAVING IMPROVED STABILITY, ENHANCED IMMUNOGENICITY AND REDUCED REACTOGENICITY AND PROCESS FOR PREPARATION THEREOF

(71) Applicant: SERUM INSTITUTE OF INDIA PVT LTD., Maharashtra (IN)

(72) Inventors: Rakesh Kumar, Maharashtra (IN); Inder Jit Sharma, Maharashtra (IN); Anil Vyankatrao Shitole, Maharashtra (IN); Manohar Doddapaneni, Maharashtra (IN); Hitt Jyoti Sharma, Maharashtra (IN)

(73) Assignee: SERUM INSTITUTE OF INDIA PVT LTD, Maharashtra (IN)

(*) Notice: Subject to any disclaimer, the term of this patent is extended or adjusted under 35 U.S.C. 154(b) by 0 days.

(21) Appl. No.: 16/631,965

(22) PCT Filed: Jul. 13, 2018

(86) PCT No.: PCT/IB2018/055180
§ 371 (c)(1),
(2) Date: Jan. 17, 2020

(87) PCT Pub. No.: WO2019/016654
PCT Pub. Date: Jan. 24, 2019

(65) Prior Publication Data

US 2020/0206331 A1 Jul. 2, 2020

(30) Foreign Application Priority Data

Jul. 18, 2017 (IN) ............................ 201721025513

(51) Int. Cl.
*A61K 39/00* (2006.01)
*A61K 39/102* (2006.01)
*A61K 39/13* (2006.01)
*A61K 39/29* (2006.01)

(52) U.S. Cl.
CPC ........ *A61K 39/0018* (2013.01); *A61K 39/102* (2013.01); *A61K 39/13* (2013.01); *A61K 39/292* (2013.01); *A61K 2039/5252* (2013.01); *A61K 2039/55505* (2013.01); *A61K 2039/70* (2013.01)

(58) Field of Classification Search
None
See application file for complete search history.

(56) References Cited

U.S. PATENT DOCUMENTS 6,013,264 A 1/2000 Petre et al.
8,945,582 B2 * 2/2015 De Hemptinne ...... A61K 39/12 424/201.1

FOREIGN PATENT DOCUMENTS

| | | | | |
|---|---|---|---|---|
| EP | 1 028 750 | A1 | 8/2000 | |
| EP | 1 307 473 | A1 | 5/2003 | |
| WO | 93/24148 | A1 | 12/1993 | |
| WO | 97/00697 | A1 | 1/1997 | |
| WO | 99/13906 | A1 | 3/1999 | |
| WO | 99/48525 | A1 | 9/1999 | |
| WO | 00/30678 | A1 | 6/2000 | |
| WO | 02/12287 | A1 | 2/2002 | |
| WO | 2004/110480 | A2 | 12/2004 | |
| WO | 2005/089794 | A2 | 9/2005 | |
| WO | 2008/028956 | A1 | 3/2008 | |
| WO | 2010/046934 | A1 | 4/2010 | |
| WO | WO-2010046934 | A1 * | 4/2010 | ........... A61K 39/102 |
| WO | 2012/093406 | A2 | 7/2012 | |
| WO | 2017/048038 | A1 | 3/2017 | |

OTHER PUBLICATIONS

Weigand et al., 2016 (Complete Genome Sequences of Four Bordetella pertussis Vaccine Reference Strains from Serum Institute of India; Genome Announcements 4(6):e01404-16); (Year: 2016).*

* cited by examiner

*Primary Examiner* — Mary Maille Lyons
(74) *Attorney, Agent, or Firm* — BakerHostetler

(57) ABSTRACT

An immunogenic composition comprising of Diphtheria toxoid antigen (D), tetanus toxoid (T) antigen, Hepatitis B surface antigen (HBsAg), inactivated whole-cell *B. pertussis* (wP) antigen, *Haemophilus influenzae* type B (Hib) capsular saccharide conjugated to a carrier protein, Inactivated Polio Virus (IPV) antigen and additionally one or more antigens and the method of preparing the same. A fully liquid combination vaccine, showing improved immunogenicity, reduced reactogenicity and improved stability. Improved methods of formaldehyde inactivation, improved adsorption profile of Diphtheria toxoid antigen (D), tetanus toxoid (T) antigen and Hepatitis B (HepB) surface antigen adsorbed individually onto aluminium phosphate adjuvant, minimum total aluminum content ($Al^{3+}$) and optimized concentration of 2-phenoxyethanol (2-PE) as preservative.

9 Claims, No Drawings

IMMUNOGENIC COMPOSITION HAVING IMPROVED STABILITY, ENHANCED IMMUNOGENICITY AND REDUCED REACTOGENICITY AND PROCESS FOR PREPARATION THEREOF

CROSS-REFERENCE TO RELATED APPLICATIONS

This application is a National Stage of International patent application PCT/M2018/055180, filed on Jul. 13, 2018, which claims priority to foreign Indian patent application No. IN 201721025513, filed on Jul. 18, 2017, the disclosures of which are incorporated by reference in their entirety.

TECHNICAL FIELD

The present disclosure relates to the field of biotechnology, more particularly, it relates to a combination vaccine composition comprising of a group of antigens/immunogens and the method of preparing the same. The present disclosure further relates to an improved methodology in the field of combination vaccine production.

BACKGROUND

A combination vaccine which can provide immunogenicity against a large number of diseases is always advantageous over the monovalent vaccine since it reduces the number of shots given, reduced complications associated with multiple intramuscular injections, reduces the administration and production costs, decreased costs of stocking, reduced risk of delayed or missed vaccinations and improves the patient compliance by reducing the number of separate vaccinations. Moreover, the fully liquid preparations of combination vaccine have distinct advantages over those which require reconstitution. Average preparation time is found to be almost half for the fully-liquid vaccine compared the non-fully-liquid vaccine. In the same study, almost all health care personnel (97.6%) stated that they would prefer the use of the fully-liquid vaccine in their daily practice. (Ref: Soubeyrand B, et al; Assessment of preparation time with fully-liquid versus non-fully liquid paediatric hexavalent vaccines. A time and motion study; Vaccine 2015; 33:3976-82).

The currently known and available combination vaccines may not contain appropriate formulations of appropriate antigens in appropriate immunogenic forms for achieving desired levels of safety, efficacy and immunogenicity in the susceptible human population for a number of diseases in one shot. The number of different vaccine combinations that can be created with just a few additional antigens is considerable. By adding 1 to 4 other antigen components (e.g. HIB (freeze-dried or liquid), HBV, IPV, HAV) to either DTwP or DTaP, there are 44 possible different vaccine combinations that can be generated. The number would increase to thousands if individual components from different manufacturers were considered. As every individual new combined vaccine (taking into account differences in components according to source) must be developed separately to demonstrate safety, stability, compatibility and efficacy the development of all these vaccines becomes a challenging task.

Antigens of the Combination Vaccine:

Diphtheria and Tetanus Antigens

Diphtheria and tetanus are acute infections caused by *Cornyebacterium Diphtheriae* and *Clostridium tetani*, respectively. In both instances it is a potent exotoxin of these bacteria's that is responsible for clinical disease. The vaccines affording protection against these bacteria contain these toxins which are chemically modified hence are no longer toxic but is still antigenic. Diphtheria and Tetanus toxin are produced by growing *Corynebacterium Diphtheriae* and *Clostridium tetani*, in a medium containing bovine extract. The toxins are inactivated using following treatment that include Heat, UV, Formalin/Formaldehyde, glutaraldehyde, Acetylethyleneimine, etc. for making toxoids [Diphtheria toxoid (D) and Tetanus toxoid (T)]. Concerns with respect to Bovine spongiform encephalopathy (BSE), Transmissible spongiform encephalopathy (TSE), Creutzfeldt-Jakob disease (CJD and variant CJD diseases) may arise from animal components used in the growth medium containing bovine extract spreading through the vaccine. (Ref: WHO Guidelines on Transmissible Spongiform Encephalopathies in relation to Biological and Pharmaceutical Products; 2003 & EMEA/CPMP/BWP/819/01; 24 Apr. 2001), Pertussis Antigens The introduction of whole-cell vaccines composed of chemically- and heat-inactivated *Bordetella pertussis* organisms in the 1940's was responsible for a dramatic reduction in the incidence of whooping cough caused by *B. pertussis*.

Whole-cell DTP vaccines are commonly associated with several local adverse events (e.g., erythema, swelling, and pain at the injection site), fever, and other mild systemic events (e.g., drowsiness, fretfulness, and anorexia) (Ref: Cody C L, Baraff L J, Cherry J D, Marcy S M, Manclarck C R; The nature and rate of adverse reactions associated with DTP and DT immunization in infants and children. Paediatrics 1981; 68:650-60) & (Ref: Long S S, DeForest A, Pennridge Pediatric Associates, et al. Longitudinal study of adverse reactions following Diphtheria-tetanus-pertussis vaccine in infancy. Paediatrics 1990; 85:294-302). More severe systemic events (e.g., convulsions {with or without fever} and hypotonic hyporesponsive episodes) occur less frequently (ratio of one case to 1,750 doses administered) among children who receive whole-cell DTP vaccine (Ref: Cody C L, Baraff L J, Cherry J D, Marcy S M, Manclarck C R; The nature and rate of adverse reactions associated with DTP and DT immunization in infants and children. Paediatrics 1981; 68:650-60). Acute encephalopathy occurs even more rarely (ratio of 0-10.5 cases to one million doses administered). Experts do agree that whole-cell pertussis vaccine causes lasting brain damage in some rare cases. (Ref: Institute of Medicine; DPT vaccine and chronic nervous system dysfunction, a new analysis; Washington D.C., National Academy Press, 1994).

Several reports citing a relationship between whole-cell pertussis vaccination, reactogenicity and serious side-effects led to a decline in vaccine acceptance and consequent renewed epidemics (Miller, D. L., Ross, E. M., Alderslade, R., Bellman, M. H., and Brawson, N. S. B. (1981). Pertussis immunization and serious acute neurological illness in children: Brit Med. J. 282: 1595-1599).

Whole cell pertussis (wP) related adverse reactions are a hindrance for their continued use worldwide and therefore wP based combination vaccines were gradually replaced by acellular pertussis based combination vaccines in the industrialized world. More recently, defined component pertussis vaccines have been developed. All liquid hexavalent acellular pertussis based vaccines (DTaP IPV PRP-T-HBsAg) have been previously reported (EP1028750).

Infanrix® Hexa (GSK) is presently the only globally marketed hexavalent pediatric combination vaccine containing Salk IPV. This product (DTaP3-IPV-HBV//Hib) is sold as a prefilled syringe of the pentavalent product co-packaged with a lyophilized Hib antigen PRP-T conjugate in a separate vial to be reconstituted with the rest of the vaccine before use.

A second hexavalent vaccine, Hexyon® (also called Hexacima® and Hexaxim®) is an all-liquid hexavalent from Sanofi Pasteur; however it is also with aP, This vaccine is likely to be targeted for private markets in Europe and worldwide. Another hexavalent vaccine, also with aP, which is being jointly developed by Merck and Sanofi Pasteur, is currently in Phase III clinical studies.

A heptavalent combination vaccine is being developed by Bharat Biotech International that consists of DT, Acellular pertussis, Sabin IPV (type 1: 40 DU, type 2:8 DU, type 3:32DU), Single strain inactivated Rotavirus (G9 strain i.e 116E strain), a conjugate *Haemophilus* influenza type b PRP conjugate to TT and a Recombinant Hepatitis B vaccine.

However there have been emerging concerns about the long-term effectiveness of acellular pertussis (aP) vaccines, especially in developing-country settings. Recent reports suggest that immunity to pertussis wanes in adolescence and that this is responsible for an increase in cases in infants under six months of age, before they are fully vaccinated. Vaccine efficacy was estimated to be 24 percent in 8 to 12 year old immunized in infancy with aP. An observational study in Australia also showed higher case rates among adolescents given aP vaccine in infancy than among those given wP vaccine (relative risk of 3.3, 95 percent confidence interval 2.4-4.5).

From a cost perspective, aP antigens have historically exceeded the cost of wP antigens by a factor of 10 to 30 due to manufacturing differences and royalty costs and hence constitute an economic burden to developing countries. As a result, the cost of wP-based hexavalent vaccines would be better suited for use in the public sector of low-resource countries.

Hence, the use of Whole cell pertussis (wP) in hexavalent vaccines intended for developing countries has become important both because of cost and emerging concerns about the long-term effectiveness of aP vaccines, especially in developing-country settings. Compared with the best whole-cell pertussis (wP) vaccines, aP vaccines are not as effective in mass immunization programs (Vickers et al. 2006; Cherry 2012), Recent studies of outbreaks in highly immunized populations have shown that the duration of protection of aP vaccines is too short (Klein et al. 2012; Misegades et al. 2012), resulting in a decrease in immunity in older children and adolescents, and a corresponding increase in cases in this age group (Skowronski et al. 2002; Klein et at 2012). This is in contrast to wP vaccines, which provide protection well into the teenaged years (Klein et al. 2012). As a result of these shortcomings, in countries that switched to the aP vaccine in the 1990s we now have a generation of children not only less well-protected against pertussis but who may also be less responsive to boosters, since the vaccine with which a child is primed may determine their immune response to later booster vaccination (Podda et al. 1995; Mascart et al, 2007; Sheridan et al. 2012; Liko, Robison and Cieslak 2013; Smits et al. 2013).

One of the most important factors that contribute to the reactogenicity of wP is the presence of lipo-oligosaccharide (LOS), the endotoxin from the bacterial outer membrane.

The inactivation of toxins in wP vaccines can be done by various methods, but no active heat labile toxin should be detectable in the final product. The whole cell pertussis (wP) bulk process for inactivation of wP toxins practiced by many manufacturers use heat treatment/formalin. Several reports cite use of Thimerosal for inactivation of wP. However, use of Thimerosal causes loss of antigenicity of IPV (Vaccine 1994 Volume 12 No. 9 851-856. Deleterious effect of thimerosal on the potency of inactivated poliovirus vaccine), and therefore in case of a combination vaccine containing IPV, may need to be presented in a separate vial from thimerosal-containing wP to retain its potency over time or changing the source pertussis bulk inactivation. Some antigens i.e. active PT may also serve as immune response modifiers, and significant differences in immune responses to various antigens between different vaccines have been observed (WHO, 1993).

Chemical extraction of LOS resulted in a significant decrease in endotoxin content (20%) and a striking decline in endotoxin related toxicity (up to 97%), depending on the used in vitro or in vivo test. The LOS extraction did not affect the integrity of the product and, more importantly, did not affect the potency and/or stability of DTP low. Moreover, hardly any differences in antibody and T-cell responses were observed. (Ref: Waldely Oliveira Dias et. al; An improved whole cell pertussis vaccine with reduced content of endotoxin; Human Vaccines & Immunotherapeutics 9:2, 339-348; February 2012)

Hepatitis B Antigens

There are various strains of Hepatitis virus. Hepatitis B is a disease caused by hepatitis B virus (HepB) which infects the liver of humans, and causes an inflammation called hepatitis. The vaccine against the disease contains one of the viral envelope proteins, hepatitis B surface antigen (HBsAg). Vaccines which have been used for mass immunization are now available, for example the product Recombivax HB® and Comvax® by Merck, Engerix-B® and Pediarix® by Glaxo SmithKline Biologicals. Combination vaccine having Hepatitis B component was associated with both higher completion and compliance outcomes compared with HepB single-antigen vaccine. (Ref: Kurosky. et. al; Effect of Combination Vaccines on Hepatitis B Vaccine Compliance in Children in the United States; The Pediatric Infectious Disease Journal, 36(7):e189-e196, July 2017). Several references cite adsorption of Hepatitis B surface antigen onto aluminium phosphate in combination with other antigens. The Hepatitis B component should be substantially thiomersal free (method of preparation of HBsAg without thiomersal has been previously published in EP1307473). Hexavac® a combination vaccine that was withdrawn from the market due to low immunogenicity of the hepatitis B component. There is therefore a need for a combination vaccine composition comprising a Hepatitis B antigen with adequate or enhanced immunogenicity.

*Haemophilus influenzae* (Hib) Antigens

*Haemophilus influenzae* is a Gram-negative coccobacillus that is a normal part of upper respiratory tract flora. *Haemophilus influenzae* type b (Hib b) is a major cause of meningitis invasive blood borne infections in young children and major cause of meningitis in the first 2 years of life. Immunization against *Haemophilus influenzae* began in Canada in 1987 with a polysaccharide vaccine [polyribose ribitol phosphate (PRP)]. The polyribosylribitol phosphate (PRP) capsule of Hib is a major virulence factor for the organism. Antibody to PRP is the primary contributor to serum bactericidal activity, and increasing levels of antibody are associated with decreasing risk of invasive disease. PRP is a T-cell independent antigen and hence is characterized by a) induction of a poor antibody response in less than 18-month-old infants and children, b) a variable and quantitatively smaller antibody response than that seen with T-cell dependent antigens, c) production of a higher proportion of immunoglobulin M (IgM), and d) inability to induce a booster response.

The initial vaccines based only on the PRP component proved to be ineffective in the infants. Further efforts were directed towards the PRP conjugate vaccine, wherein the PRP is conjugated to proteins called the carrier proteins such as the outer membrane protein of *Neisseria meningitides*, Diphtheria toxoid, Tetanus toxoid and CRM 197. The inclusion of Hib-conjugate components in combination vaccines has been associated with reduced Hib immunogenicity. Furthermore, the Hib-conjugates are unstable in aqueous media and cannot survive prolonged storage in this form. Hence, the PRP polysaccharide of *Haemophilus influenzae* b (Hib) is frequently formulated as a dried solid, which is reconstituted at the time of delivery with a liquid formulation of the other antigens. For example in Infanrix® hexa (WO99/48525).

Poliomyelitis Antigen

Different kinds of vaccine are available:

A live attenuated (weakened) oral polio vaccine (OPV) developed by Dr. Albert Sabin in 1961. OPV, comprising the Sabin strains, is given orally.

An inactivated (killed) polio vaccine (IPV) developed in 1955 by Dr. Jonas Salk. IPV, comprising the Salk strains, is given as an injection.

Recently, the Sabin inactivated polio virus, which was prepared by inactivating the Sabin strains polio virus with formalin, has been developed for injection and also has been available in commercial products.

Both live attenuated (OPV) and inactivated (IPV) polio vaccines have been effective in controlling the polio disease worldwide. The polio vaccine may comprise the Salk or the Sabin strains, In 1955, Dr. Jonas Salk succeeded in inactivation of the wild type polio virus, thus enabling it in an injection type formulation, and named it as the Salk strain, which includes Mahoney type 1, MEF type 2, and Saukett type 3 that have been used in the vaccine against the poliomyelitis disease. The Sabin strains include the Sabin 1 and Sabin 2 strains.

The currently acceptable standard dose of polio vaccines contains 40 D antigen units of inactivated poliovirus type 1 (Mahoney), 8 D antigen units of inactivated poliovirus type 2 (MEF-I) and 32 D antigen units of inactivated poliovirus type 3 (Saukett) e.g. Infanrix-Hexa® (WO99/48525).

IPV is currently available either as a non-adjuvanted stand-alone formulation, or in various combinations, including DT-IPV (with Diphtheria and tetanus toxoids) and hexavalent-IPV vaccines (additionally with pertussis, hepatitis B, and *Haemophilus influenzae* b) e.g. Infanrix® hexa (WO99/48525).

However, when compared to OPV, the overall production cost for IPV is significantly higher. This is mainly due to requirements for: (i) more virus per dose; (ii) additional downstream processing (i.e. concentration, purification and inactivation), and the related QC-testing (iii) loss of antigen or poor recovery in downstream and iv) containment. Until now, the financial challenge has been a major drawback for IPV innovation and implementation in low and middle-income countries.

The future global demand for IPV following eradication of polioviruses could increase from the current level of 80 million doses to 450 million doses per year. Consequently, approaches to “stretch” supplies of IPV are likely to be required. Reduced-dose efficacious vaccine formulations which provide protection against infection using a lower dose of IPV antigen are desirable in situations where the supply of conventional vaccine is insufficient to meet global needs or where the cost of manufacture of the conventional vaccine prevents the vaccine being sold at a price which is affordable for developing countries. Also the exposure to lower dose of IPV; compared to the existing marketed formulations could be more safer. Thus various strategies to make IPV available at more affordable prices need to be evaluated. Consequently a combination vaccine comprising dose reduced IPV could make it further cheap and easy to administer.

In case of pandemic influenza vaccines the use of adjuvants has permitted dose reduction, increased the availability and reduced cost of the vaccine. Therefore, it has been speculated that an adjuvanted vaccine formulation of IPV would reduce cost and also increase the number of available IPV doses worldwide.

Further, Aluminum salts have been considered safe, are already being used in combination vaccines containing IPV, have the lowest development hurdles and are inexpensive to manufacture. However aluminium adjuvants are not known for permitting significant dose-reduction.

Other Antigens

The other antigens that could be included in to combination vaccine are *Haemophilus influenzae* (a, c, d, e, f serotypes and the unencapsulated strains), Hepatitis (A, C, D, E, F and G strains), meningitis A, B or C, Influenza, Pneumococci, Streptococci, anthrax, dengue, malaria, measles, mumps, rubella, BCG, Japanese encephalitis, Rotavirus, smallpox, yellow fever, typhoid, Singles, Varicella virus, and others.

The range and the type of antigens used in a combination vaccine depend upon the target population age to be used such as infants, toddlers, children, adolescents, and adults. The earliest known combination vaccine which could prevent infection from *Bordetella pertussis, Clostridium tetani, Corynebacterium Diphtheriae*, and optionally inactivated poliovirus (IPV), and/or Hepatitis B virus, and/or *Haemophilus influenzae* type B infection are known (see for instance WO 93/24148, WO97/00697, WO2000/030678, WO2008/028956, U.S. Pat. No. 6,013,264 & WO2005089794).

Meanwhile, a multiple-dose vaccine injection must use a preservative to avoid contamination by microorganisms. For the combination vaccine products exported to less-developed countries by the UN, etc., multiple-dose vaccines containing a preservative are preferred, considering the environments of the countries where the vaccines are to be used, methods of distribution, expenses, etc. Examples of the preservative to be used in the vaccine products may contain thimerosal, 2-PE, phenol, formaldehyde, and conventional doses of the preservatives are known in the art.

The Inventors have found that the immunogenicity, reactogenicity, stability and the maintenance of the right form of the antigens in a combination vaccine composition depend on the way the composition has been formulated that include the process of making individual antigens, sequence of addition of the antigens, the use of the specific adjuvants in a specific quantity for certain antigens, individual adsorption or combined adsorption of antigens onto adjuvants, Degree of adsorption of antigen onto adjuvants, total Alum content, concentration and type of preservative used, the use of various parameters including agitation, temperature and pH.

SUMMARY OF INVENTION

A liquid, stable combination vaccine composition showing improved immunogenicity and reduced reactogenicity and process of making thereof is disclosed.

The present disclosure relates to a combination vaccine composition comprising of— a) A highly purified Diphtheria toxoid (D) & tetanus toxoid (T) produced using semi synthetic medium and subsequently detoxified.

b) Inactivated whole-cell *B. pertussis* (wP) component prepared using a combination of heat and chemical inactivation, specific *Bordetella pertussis* strains in a particular ratio resulting in reduced reactogenicity and increased potency.

c) *Haemophilus influenzae* type B (Hib) capsular polysaccharide antigen (PRP) conjugated to a carrier protein (CP)

d) Standard Dose or Dose reduced Salk or Sabin (Inactivated Polio Virus) IPV prepared by utilizing improved methods of formaldehyde inactivation and may further be adsorbed onto aluminium hydroxide.

e) Optimal adsorption profile of antigen(s) such that Hepatitis B (HepB) surface antigen is adsorbed individually onto aluminium phosphate adjuvant, D and T antigens are individually adsorbed onto aluminium phosphate adjuvant thereby resulting in enhanced immunogenicity f) Minimum alum content thereby ensuring reduced reactogenicity g) Optimal concentration of 2-phenoxyethanol (2-PE) as preservative.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a liquid, stable, less reactogenic and more immunogenic combination vaccine composition/formulation suitable for the prevention and treatment of more than one disease state and meets the criterion for the seroprotection for each of the said immunogenic components.

Yet another object of the present disclosure is to provide a method for manufacturing such composition/formulation of the combination vaccine.

Other objects and advantages of the present disclosure will be more apparent from the following description, which is not intended to limit the scope of the present disclosure.

DETAILED DESCRIPTION

According to a first embodiment of the present disclosure, the combination vaccine composition comprise of a group of antigens/immunogens selected from but not limited to Diphtheria toxoid (D), Tetanus toxoid (T), Whole cell *B. pertussis* (wP), *Haemophilus influenzae* type B(Hib) PRP-CP conjugate, Hepatitis B (HepB), Inactivated Polio Virus (IPV) and additionally comprise of aluminium based adjuvant & preservatives.

According to a second embodiment of the present disclosure, the combination vaccine composition could further comprise of one or more antigens selected from the group consisting of but not limited to *Haemophilus influenzae* (a, c, d, e, f serotypes and the unencapsulated strains), Hepatitis (A, C, D, E, F and G strains), meningitis A, B, C, Y, W-135, or X, Influenza, *Staphylococcus aureus, Salmonella typhi* antigen(s), acellular pertussis antigen, modified adenylate cyclase, Malaria Antigen (RTS,S), Pneumococci, Streptococci, anthrax, dengue, malaria, measles, mumps, rubella, BCG, Human papilloma virus, Japanese encephalitis, Dengue, Zika, Ebola, Chikungunya, Rotavirus, smallpox, yellow fever, Flavivirus, Shingles, Varicella virus antigens respectively.

According to a third embodiment of the present disclosure, the IPV strains used in the combination vaccine composition comprise of inactivated Sabin strains selected from the group of type 1, type 2, and type 3 or inactivated Salk strains selected from the group of Mahoney type 1, MEF type 2 and Saukett type 3.

In one of the aspects of the third embodiment, Polio virus may be grown by following method:

CCL81-VERO (Monkey kidney) cell line was used as host cells for the growing of polio viruses i.e. sabin and salk strains.

After infection of host cells with desired strain of polio virus and incubation of 72 hours, the medium containing the virus and cell debris was pooled and collected in a single container.

The filtrate was subjected to tangential flow filtration with 100 KDa cassette; diafiltered using phosphate buffer and purified using anion exchange chromatography.

Prior to administration to patients, the viruses must be inactivated using appropriate inactivation methods.

However, the present inventors have surprisingly found that the high percentage loss of D-antigen post-formaldehyde inactivation could be due to presence of phosphate buffer that unexpectedly causes undesirable aggregation of polio virus particles.

Hence, an important aspect of the present disclosure comprise of, an improved process of formalin inactivation comprising of following steps:

a) The purified virus pool was subjected to buffer exchange from Phosphate buffer to Tris buffer in the range of (30 to 50 mM) having pH between 7 to 7.5, b) To the above mixture M-199 medium containing glycine (5 gm/1) was added c) 0.025% formaldehyde was added and subsequently mixed, d) The mixture was subsequently incubated at 37° C. for 5 to 13 days with continuous stirring of virus bulk on magnetic stirrer, e) The post-incubation mixture was subjected to intermediate TFF system (100 KDa, 0.1 $m^2$) on day 7 and final filtration after inactivation f) Subsequently the filtered bulk was stored at 2-8° C., g) Performing D-Ag ELISA for D-Ag unit determination According to a fourth embodiment of the present disclosure, the IPV strains used in the combination vaccine composition comprise of dose reduced inactivated Sabin strains selected from the group of type 1, type 2, and type 3 or inactivated Salk strains selected from the group of Mahoney type 1, MEF type 2 and Saukett type 3.

According to a fifth embodiment of the present disclosure, the IPV (Sabin & Salk Strains) is not adsorbed onto any adjuvant (e.g. before mixing with other components if present).

According to a sixth embodiment of the present disclosure, the IPV (Sabin & Salk Strains) component(s) may be adsorbed onto an adjuvant selected from the group of aluminium salt (Al3+) such as aluminium hydroxide ($Al(OH)_3$) or aluminium phosphate ($AlPO_4$), alum, calcium phosphate, MPLA, 30-MPL, QS21, a CpG-containing oligodeoxynucleotide adjuvant, liposome, or oil-in-water emulsion or a combination thereof. (e.g. before or after mixing with other components if present). If adsorbed, one or more IPV components may be adsorbed separately or together as a mixture on Alum hydroxide.

The IPV (Sabin & Salk Strains) component(s) may be adsorbed onto an aluminium salt by following procedure:

- Taking the desired volume of autoclaved $Al(OH)_3$ to get the final Alum (Al+++) concentration between 0.1 to 0.8 mg/dose in a 50 ml container
- Adding 1PV bulk with adjusted D-Ag unit and making up the volume with diluent (10× M-199+0.5% Glycine),
- Adjusting the final formulation pH and obtaining final formulation with pH between 6 and 6.8.

In one of the aspect of the sixth embodiment, adsorption of formalin inactivated IPV can be done on Alum ($Al^{3+}$) having concentration selected from 0.1 mg/dose, 0.2 mg/dose, 0.3 mg/dose, 0.4 mg/dose, 0.5 mg/dose, 0.6 mg/dose, 0.7 mg/dose and 0.8 mg/dose, preferably between 0.1 mg/dose to 1.25 mg/dose per serotype and at a pH selected from 6.2, 6.3, 6.4, 6.5, 6.6, 6.7 and 6.8 preferably 6.5.

In a yet another aspect of the sixth embodiment, the percent recovery of 0-Antigen post formalin inactivation in presence of Tris could be either 50%, 60%, 70% or 80% and percent adsorption post aluminium hydroxide adsorption could be between 70% to 80%, 80% to 90% or 90% to 99% or 95% to 99%.

According to a seventh embodiment of the present disclosure, Diphtheria toxin (exotoxin) and tetanus toxin (exotoxin) were obtained from *Corynebacterium Diphtheria* and *Clostridium tetani* respectively and subsequently detoxified using a suitable inactivation method. The Diphtheria toxoid (D) and Tetanus toxoid (T) thus obtained was further purified using Gel filtration chromatography. The purified DT thus obtained was further used for formulation of combination vaccine.

In one of the aspect of the seventh embodiment, Diphtheria toxin is produced by growing *Corynebacterium Diphtheriae* in a semi synthetic medium consisting of following ingredients at optimal concentrations in any one of the following combinations:

Combination 1:

Casein Hydrolysate, Maltose Monohydrate, Glacial Acetic acid, Sodium lactate, Magnesium Sulphate, β-alanine, Pimelic acid, Nicotinic acid, Cupric Sulphate, Zinc Sulphate, Manganous Chloride, L-Cystine, Calcium Chloride Dihydrate, Potassium Dihydrogen Orthophosphate, Di Potassium Hydrogen Phosphate, Ferrous Sulphate and WFI.

Combination 2:

Casein Hydrolysate, Maltose Monohydrate, Glacial Acetic acid, Sodium lactate, Magnesium Sulphate, β-alanine, Pimelic acid, Nicotinic acid, Manganous Chloride, L-Cystine, Calcium Chloride Dihydrate, Potassium Dihydrogen Orthophosphate, Di Potassium Hydrogen Phosphate, Ferrous Sulphate and WFI.

Combination 3:

Casein Hydrolysate, Maltose Monohydrate, Glacial Acetic acid, Sodium lactate, β-alanine, Pimelic acid, Nicotinic acid, Cupric Sulphate, Zinc Sulphate, Manganous Chloride, L-Cystine, Calcium Chloride Dihydrate, Potassium Dihydrogen Orthophosphate, Di Potassium Hydrogen Phosphate, and WFI.

Combination 4:

Yeast extract, Maltose Monohydrate, Glacial Acetic acid, Sodium lactate, Magnesium Sulphate, β-alanine, Pimelic acid, Nicotinic acid, Cupric Sulphate, Zinc Sulphate, Manganous Chloride, L-Cystine, Calcium Chloride Dihydrate, Potassium Dihydrogen Orthophosphate, Di Potassium Hydrogen Phosphate, Ferrous Sulphate and WFI.

According to second aspect of the seventh embodiment, Tetanus toxin is produced by growing *Clostridium tetanus* in a semi synthetic medium consisting of following ingredients at optimal concentrations in any one of the following combinations:

Combination 1:

Casein Digest, Calcium Chloride, Di Potassium Hydrogen Phosphate, Anhydrous Dextrose, Sodium chloride, Magnesium sulfate, Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI Combination 2:

Casein Digest, Calcium Chloride, β-alanine Di Potassium Hydrogen Phosphate, Anhydrous Dextrose, Sodium chloride, Magnesium sulfate, Ferrous Sulphate, Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI Combination 3:

Casein Digest, Calcium Chloride, Di Potassium Hydrogen Phosphate, Anhydrous Dextrose, Sodium chloride, Zinc Sulphate, Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI Combination 4:

Casein hydrolysate, Calcium Chloride, Di Potassium Hydrogen Phosphate, Anhydrous Dextrose, Sodium chloride, Magnesium sulfate, Manganous Chloride Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI In a yet another aspect of the seventh embodiment, the Diphtheria and tetanus toxin was detoxified using one or combination of following inactivation methods that include Heat, UV, Formalin/Formaldehyde, Acetylethyleneimine, etc.

According to an eighth embodiment of the present disclosure, the Hepatitis (Hep) antigen used in the combination vaccine composition comprise of Hep antigens derived from the surface of Hepatitis B strain (HBsAg).

In one of the aspect of the ninth embodiment, HBsAg can be made by one of the following methods:

- By purifying the antigen in particulate form from the plasma of chronic hepatitis B carriers, as large quantities of HBsAg are synthesized in the liver and released into the blood stream during an HBV infection
- Expressing the protein by recombinant DNA methods According to a ninth embodiment of the present disclosure, Diphtheria toxoid (D), Tetanus toxoid (T) and Hepatitis B surface antigen (HBsAg) are individually adsorbed on to adjuvant selected from the group of aluminium salt (Al3+) such as aluminium hydroxide ($Al(OH)_3$) or aluminium phosphate ($AlPO_4$), alum, calcium phosphate, MPLA, 3D-MPL, QS21, a CpG-containing oligodeoxynucleotide adjuvant, liposome, or oil-in-water emulsion or a combination thereof.

Yet preferably Diphtheria toxoid (D), Tetanus toxoid (T) and Hepatitis B surface antigen (HBsAg) are individually adsorbed on to aluminum phosphate.

In one of the aspect of the ninth embodiment, the Diphtheria toxoid (D) antigen adsorbed on to aluminium phosphate having percentage adsorption of at least 50%, In another aspect of the ninth embodiment, the tetanus toxoid (T) antigen adsorbed on to aluminium phosphate having percentage adsorption of at least 40%.

In a yet another aspect of the ninth embodiment, the Hepatitis B surface antigen (HBsAg) adsorbed on to aluminium phosphate having percentage adsorption of at least 70%.

According to a tenth embodiment of the present disclosure, the Hib antigen used in the combination vaccine of the present disclosure is derived from the capsular polysaccharide of Hib b strain 760705.

According to one aspect of the tenth embodiment, the Hib b PRP antigen is conjugated to a carrier protein selected from a group of carrier protein consisting of but not limited to CRM197, Diphtheria toxoid, *Neisseria meningitidis* outer membrane complex, fragment C of tetanus toxoid, pertussis toxoid, protein D of *H. influenzae, E. coli* LT, *E. coli* ST, and exotoxin A from *Pseudomonas aeruginosa*, outer membrane complex c (OMPC), porins, transferrin binding proteins, pneumolysin, pneumococcal surface protein A (PspA), pneumococcal surface adhesin A (PsaA), pneumococcal PhtD, pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD), synthetic, peptides, heat shock proteins, pertussis proteins, cytokines, lymphokines, hormones, growth factors, artificial proteins comprising multiple human CD4+ T cell epitopes from various pathogen-derived antigens such as N 19, iron-uptake proteins, toxin A or B from *C. difficile* and *S. agalactiae* proteins.

Yet preferably the Hib b PRP is conjugated to tetanus toxoid (TT). by CNBr chemistry, Reductive amination chemistry, Cyanylation chemistry or any other chemistry already discloses in Kniskern et al., "Conjugation: design, chemistry, and analysis" in Ellis et al., Development and clinical uses of *Haemophilus* b conjugate vaccines. New York: Marcel Dekker, 1994: 37-69

According to second aspect of the tenth embodiment, the carrier protein is present in both free and conjugated form in a composition of the present disclosure, the unconjugated form is preferably no more than 20% of the total amount of the carrier protein in the composition as a whole, and more preferably present at less than 5% by weight.

According to third aspect of the tenth embodiment, the Hib antigen is not substantially adsorbed on to any adjuvant.

According to fourth aspect of the tenth embodiment, the Hib antigen may not be subjected to deliberate or intentional adsorption on any adjuvant.

According to an eleventh embodiment of the present disclosure, whole cell pertussis (wP) antigen preparation used in the combination vaccine composition of the present disclosure is preferably made from *Bordetella pertussis* strains 134, 509, 25525 and 6229 mixed in a specific ratio and subsequently inactivated by utilizing improved methods of inactivation devoid of thimerosal hence leading to reduced reactogenicity & increased potency and may or may not be adsorbed onto aluminium based adjuvants.

According to one aspect of the eleventh embodiment, whole cell pertussis (wP) antigen preparation used in the combination vaccine composition of the present disclosure is preferably made from *Bordetella pertussis* strains 134, 509, 25525 and 6229 mixed in a ratio of 1:1:0.25:0.25.

According to second aspect of the eleventh embodiment, whole cell pertussis (wP) antigen preparation used in the combination vaccine composition was inactivated using one or more of following inactivation treatment that include Heat, UV, Formalin/Formaldehyde, Acetylethyleneimine, etc.

Yet preferably whole cell pertussis (wP) antigen preparation used in the combination vaccine composition was inactivated using a combination of heat and chemical treatment. Yet preferably heat inactivated at 56±2° C., 10 to 15 mins in presence of formaldehyde wherein, wP bulk remains non-clumpy and easily homogenized thereby leading to reduced reactogenicity and giving better wP potency for a longer duration.

According to third aspect of the eleventh embodiment, whole cell pertussis (wP) antigen preparation used in the combination vaccine composition may or may not be adsorbed onto an aluminium based adjuvant such as aluminium hydroxide, aluminium phosphate or combination thereof (e.g. before or after mixing with other components if present). If adsorbed, one or more wP strains (i.e. 134, 509, 25525 and 6229) may be adsorbed separately or together as a mixture.

According to a twelfth embodiment of the present disclosure, Diphtheria toxoid (D) is in an amount in the range of 1-40 Lf; Tetanus toxoid (T) is in an amount in the range of 4-25 Lf; wP is in an amount in the range of 4-30 IOU per 0.5 ml; *H. influenzae* B PRP-TT conjugate is in an amount in the range of 1-20 μg of PRP content per 0.5 ml; HBsAg antigen is in an amount in the range of 1-20 μg per 0.5 ml; Sabin IPV which includes type 1, type 2, and type 3, wherein type 1 is contained in an amount of 1-50 DU/0.5 ml, type 2 is contained in an amount of 1-20 DU/0.5 ml, and type 3 is contained in an amount of 1-50 DU/0.5 ml and additionally comprise of aluminium based adjuvant & preservatives in the final combination vaccine composition/formulation.

Yet preferably the Diphtheria toxoid (D) is in an amount of about 25 Lf in the final combination vaccine composition.

Yet preferably the Diphtheria toxoid (D) is in an amount of about 20 Lf in the final combination vaccine composition.

Yet preferably the Diphtheria toxoid (D) is in an amount of about 10 Lf in the final combination vaccine composition.

Yet preferably the tetanus toxoid (T) is in an amount of about 10 Lf in the final combination vaccine composition.

Yet preferably the tetanus toxoid (T) is in an amount of about 4 Lf in the final combination vaccine composition.

Yet preferably the tetanus toxoid (T) is in an amount of about 2 Lf in the final combination vaccine composition.

Yet preferably the wP is in an amount of about 16 IOU per 0.5 ml in the final combination vaccine composition.

Yet preferably the wP is in an amount of about 14 IOU per 0.5 ml in the final combination vaccine composition.

Yet preferably the wP is in an amount of about 12 IOU per 0.5 ml in the final combination vaccine composition.

Yet preferably the *H. influenzae* B PRP-TT conjugate is in an amount of about 13 pg of PRP content per 0.5 ml.

Yet preferably the *H. influenzae* B PRP-TT conjugate is in an amount of about 10 μg of PRP content per 0.5 ml.

Yet preferably the *H. influenzae* B PRP-TT conjugate is in an amount of about 8 μg of PRP content per 0.5 ml.

Yet preferably the HBsAg antigen is in an amount of about 15 μg per 0.5 ml in the final combination vaccine composition.

Yet preferably the HBsAg antigen is in an amount of about 10 μg per 0.5 ml in the final combination vaccine composition.

Yet preferably the HBsAg antigen is in an amount of about 8 μg per 0.5 ml in the final combination vaccine composition.

Yet preferably the Sabin inactivated polio vaccine (sIPV) which includes type 1, type 2, and type 3 strains are present in an amount of about 40 DU, 8 DU and 32 DU, respectively per 0.5 ml in the final combination vaccine composition.

According to a thirteenth embodiment of the present disclosure, Diphtheria toxoid (D) is in an amount in the range of 1-40 Lf; Tetanus toxoid (T) is in an amount in the range of 4-25 Lf; wP is in an amount in the range of 4-30 IOU per 0.5 ml; *H. influenzae* B PRP-TT conjugate is in an amount in the range of 1-20 μg of PRP content per 0.5 ml; HBsAg antigen is in an amount in the range of 1-20 ug per 0.5 ml; Salk inactivated polio virus (IPV), which includes Mahoney type 1, MEF Type 2 and the Saukett type 3 strains, wherein Mahoney type 1 is contained in an amount of 1-50 DU/0.5 ml, MEF Type 2 is contained in an amount of 1-20 DU/0.5 ml and Saukett type 3 is contained in an amount of 1-50 DU/0.5 ml and additionally comprise of aluminium based adjuvant & preservatives in the final combination vaccine composition/formulation.

Yet preferably the Diphtheria toxoid (D) is in an amount of about 25 Lf in the final combination vaccine composition.

Yet preferably the Diphtheria toxoid (D) is in an amount of about 20 Lf in the final combination vaccine composition.

Yet preferably the Diphtheria toxoid (D) is in an amount of about 10 Lf in the final combination vaccine composition.

Yet preferably the tetanus toxoid (T) is in an amount of about 10 Lf in the final combination vaccine composition.

Yet preferably the tetanus toxoid (T) is in an amount of about 4 Lf in the final combination vaccine composition.

Yet preferably the tetanus toxoid (T) is in an amount of about 2 Lf in the final combination vaccine composition.

Yet preferably the wP is in an amount of about 16 IOU per 0.5 ml in the final combination vaccine composition.

Yet preferably the wP is in an amount of about 14 IOU per 0.5 ml in the final combination vaccine composition.

Yet preferably the wP is in an amount of about 12 IOU per 0.5 ml in the final combination vaccine composition.

Yet preferably the *H. influenzae* B PRP-TT conjugate is in an amount of about 13 μg of PRP content per 0.5 ml, Yet preferably the *H. influenzae* B PRP-TT conjugate is in an amount of about 10 μg of PRP content per 0.5 ml.

Yet preferably the *H. influenzae* B PRP-TT conjugate is in an amount of about 8 μg of PRP content per 0.5 ml.

Yet preferably the HBsAg antigen is in an amount of about 15 μg per 0.5 ml in the final combination vaccine composition.

Yet preferably the HBsAg antigen is in an amount of about 10 μg per 0.5 ml in the final combination vaccine composition.

Yet preferably the HBsAg antigen is in an amount of about 8 μg per 0.5 ml in the final combination vaccine composition.

Yet preferably the Salk inactivated polio vaccine which includes Mahoney type 1, MEF Type 2 and the Saukett type 3 strains are present in an amount of about 40 DU, 8 DU and 32 DU, respectively per 0.5 ml in the final combination vaccine composition.

According to a fourteenth embodiment of the present disclosure, Diphtheria toxoid is in an amount in the range of 1-40 Lf; Tetanus toxoid is in an amount in the range of 4-25 Lf; wP is in an amount in the range of 4-30 IOU per 0.5 ml; *H. influenzae* B PRP-TT conjugate is in an amount in the range of 1-20 μg of PRP content per 0.5 ml; Hep antigen is in an amount in the range of 1-20 ug per 0.5 ml; dose reduced Sabin inactivated polio vaccine (sIPV) used in the combination vaccine composition, which includes type 1, type 2, and type 3, wherein type 1 is contained in an amount of 2.5-10 DU/0.5 ml, type 2 is contained in an amount of 5-20 DU/0.5 ml, and type 3 is contained in an amount of 1-20 DU/0.5 ml and additionally comprise of aluminium based adjuvant & preservatives in the final combination vaccine composition/formulation.

Yet preferably the Diphtheria toxoid (D) is in an amount of about 25 Lf in the final combination vaccine composition.

Yet preferably the Diphtheria toxoid (D) is in an amount of about 20 Lf in the final combination vaccine composition.

Yet preferably the Diphtheria toxoid (D) is in an amount of about 10 Lf in the final combination vaccine composition.

Yet preferably the tetanus toxoid (T) is in an amount of about 10 Lf in the final combination vaccine composition.

Yet preferably the tetanus toxoid (T) is in an amount of about 4 Lf in the final combination vaccine composition.

Yet preferably the tetanus toxoid (T) is in an amount of about 2 Lf in the final combination vaccine composition.

Yet preferably the wP is in an amount of about 16 IOU per 0.5 ml in the final combination vaccine composition.

Yet preferably the wP is in an amount of about 14 IOU per 0.5 ml in the final combination vaccine composition.

Yet preferably the wP is in an amount of about 12 IOU per 0.5 ml in the final combination vaccine composition.

Yet preferably the *H. influenzae* B PRP-TT conjugate is in an amount of about 13 μg of PRP content per 0.5 ml, Yet preferably the *H. influenzae* B PRP-TT conjugate is in an amount of about 10 μg of PRP content per 0.5 ml.

Yet preferably the *H. influenzae* B PRP-TT conjugate is in an amount of about 8 μg of PRP content per 0.5 ml.

Yet preferably the HBsAg antigen is in an amount of about 15 μg per 0.5 ml in the final combination vaccine composition.

Yet preferably the HBsAg antigen is in an amount of about 10 μg per 0.5 ml in the final combination vaccine composition.

Yet preferably the HBsAg antigen is in an amount of about 8 μg per 0.5 ml in the final combination vaccine composition.

Yet preferably the dose reduced Sabin inactivated polio vaccine (sIPV) which includes type 1, type 2, and type 3 strains are present in an amount of about 5 DU, 16 DU and 10 DU, respectively per 0.5 ml in the final combination vaccine composition.

According to a fifteenth embodiment of the present disclosure, Diphtheria toxoid is in an amount in the range of 1-40 Lf; Tetanus toxoid is in an amount in the range of 4-25 Lf; wP is in an amount in the range of 4-30 IOU per 0.5 ml; *H. influenzae* B PRP-TT conjugate is in an amount in the range of 1-20 μg of PRP content per 0.5 ml; Hep antigen is in an amount in the range of 1-20 ug per 0.5 ml; dose reduced Salk inactivated polio vaccine, which includes Mahoney type 1, MEF Type 2 and the Saukett type 3 strains, wherein Mahoney type 1 is contained in an amount of 5-15 DU/0.5 ml, MEF Type 2 is contained in an amount of 1-18 DU/0.5 ml and Saukett type 3 is contained in an amount of 5-15 DU/0.5 ml and additionally comprise of aluminium based adjuvant & preservatives in the final combination vaccine composition/formulation.

Yet preferably the Diphtheria toxoid (D) is in an amount of about 25 Lf in the final combination vaccine composition.

Yet preferably the Diphtheria toxoid (0) is in an amount of about 20 Lf in the final combination vaccine composition.

Yet preferably the Diphtheria toxoid (D) is in an amount of about 10 Lf in the final combination vaccine composition.

Yet preferably the tetanus toxoid (T) is in an amount of about 10 Lf in the final combination vaccine composition.

Yet preferably the tetanus toxoid (T) is in an amount of about 4 Lf in the final combination vaccine composition.

Yet preferably the tetanus toxoid (T) is in an amount of about 2 Lf in the final combination vaccine composition.

Yet preferably the wP is in an amount of about 16 IOU per 0.5 ml in the final combination vaccine composition.

Yet preferably the wP is in an amount of about 14 IOU per 0.5 ml in the final combination vaccine composition.

Yet preferably the wP is in an amount of about 12 IOU per 0.5 ml in the final combination vaccine composition.

Yet preferably the *H. influenzae* B PRP-TT conjugate is in an amount of about 13 μg of PRP content per 0.5 ml.

Yet preferably the *H. influenzae* B PRP-TT conjugate is in an amount of about 10 μg of PRP content per 0.5 ml.

Is Yet preferably the *H. Influenzae* B PRP-TT conjugate is in an amount of about 8 μg of PRP content per 0.5 ml, Yet preferably the HBsAg antigen is in an amount of about 15 μg per 0.5 ml in the final combination vaccine composition.

Yet preferably the HBsAg antigen is in an amount of about 10 μg per 0.5 ml in the final combination vaccine composition.

Yet preferably the HBsAg antigen is in an amount of about 8 μg per 0.5 ml in the final combination vaccine composition.

Yet preferably the dose reduced salk inactivated polio vaccine which includes Mahoney type 1, MEF Type 2 and the Saukett type 3 strains are present in an amount of about 10 DU, 2 DU and 10 DU, respectively per 0.5 ml in the final combination vaccine composition.

According to a sixteenth embodiment of the present disclosure, one or more antigens of the final combination vaccine composition may not be substantially adsorbed on to any adjuvant.

According to a seventeenth embodiment of the present disclosure, the composition comprises one or more adjuvant selected from the group of aluminium salt (Al3+) such as aluminium hydroxide ($Al(OH)_3$) or aluminium phosphate ($AlPO_4$), alum, calcium phosphate, MPLA, 3D-MPL, QS21, a CpG-containing oligodeoxynucleotide adjuvant, liposome, or oil-in-water emulsion.

Yet preferably the composition comprises aluminium phosphate ($AlPO_4$) as adjuvant.

In one of the aspect of the seventeenth embodiment, antigens of the final formulation may be adsorbed on to in situ aluminum phosphate gel or readymade aluminum phosphate gel or a combination thereof.

In one of the preferred aspect of the seventeenth embodiment, the composition of the present disclosure may contain the adjuvant in an amount of 2.5 mg/0.5 ml or less, and specifically, in an amount of 1.5 mg/0.5 ml to 0.1 mg/0.5 ml.

Yet in another preferred aspect of the seventeenth embodiment, the aluminum content (Al+3) in the final combination vaccine composition/formulation may not be more than 1.25 mg per 0.5 ml, preferably 1 mg per 0.5 ml and most preferably in an amount of 0.1 mg per 0.5 ml to 0.63 mg per 0.5 ml.

According to an eighteenth embodiment of the present disclosure, the combination vaccine composition/formulation may comprise of preservative selected from the group consisting of 2-phenoxyethanol, Benzethonium chloride (Phemerol), Phenol, Thiomersal, Formaldehyde, methyl and propyl parabens, or benzyl alcohol or a combination thereof. Yet preferably the combination vaccine composition/formulation may comprise of 2-phenoxyethanol (2-POE) as preservative.

According to one another aspect of the invention the amount of 2-phenoxyethanol in the combination vaccine of the invention may not be more than preferably 3.5 mg/0.5 ml; more preferably 3.0 mg/0.5 ml; and most preferably 2.5 mg/0.5 ml.

According to a nineteenth embodiment of the present disclosure, the combination vaccine composition/formulation of the present disclosure may contain a pharmaceutically acceptable excipients selected from the group consisting of sugars and polyols, surfactants, polymers, salts, aminoacids, pH modifiers (adjust the pH of the vaccine composition) etc. Examples of the sugars and polyols to be used may include sucrose, trehalose, lactose, maltose, galactose, mannitol, sorbitol, glycerol, etc. Examples of the surfactants may include non-ionic surfactants such as polysorbate 20, polysorbate 80, etc. Examples of the polymers may include dextran, carboxymethylcellulose, hyaluronic acid, cyclodextrin, etc. Examples of the salts may include NaCl, MgCl2, KCl, CaCl2, etc. Examples of the amino acids may include Arginine, Glycine, Histidine, etc. Examples of the pH modifiers may include sodium hydroxide, hydrochloric acid, etc.

According to a twentieth embodiment of the present disclosure, the said combination vaccine may be a lyophilized or liquid formulation, preferably liquid formulation.

According to a twenty-first embodiment of the present disclosure, the said combination vaccine may be stable at 2-8 deg C. from 12 to 36 months; at 25 deg C. from 2 to 6 months; at 37 deg C. from 1 week to 4 weeks, having final pH in the range of pH 6.0 to pH 7.0; more preferably in the range of pH 6.2 to pH 6.8; and most preferably in the range of pH 6.3 to pH 6.7.

According to a twenty-second embodiment of the present disclosure, applicant has found that a stable multivalent vaccine with improved immunogenicity and reduced reactogenicity can be obtained when vaccine is manufactured by process disclosed below taking into consideration i) process of making individual antigens ii) sequence of addition of the antigens iii) the use of the specific adjuvants in a specific quantity for certain antigens, iv) individual adsorption or combined adsorption of antigens onto adjuvants v) Degree of adsorption of antigen onto adjuvants vi) using minimum Alum concentration vii) using optimal concentration and type of preservative and viii) use of various parameters including agitation, temperature and pH.

Biological Source of Strains used in SIIPL Combination Vaccine:

Diphtheria Toxoid:

The strain *Corynebacterium diphtheriae* PW8 CN2000 was obtained from the Wellcome Research Laboratory, London, United Kingdom by the National Control Authority Central Research Institute (C.R.I.) Kasauli, Himachal Pradesh, India in lyophilized form in the year 1973. The strain was revived and further lyophilized under Master Seed Lot-*C. diphtheriae* CN2000 Al at C.R.I. Kasauli.

Tetanus Toxoid:

The strain *Clostridium tetani* Harvard Strain No. 49205 was obtained from The Rijks Institute Voor de Volksgezondheid (Netherlands) by the National Control Authority C.R.I. Kasauli, in Lyophilized form.

Pertussis:

Manufacturing of Pertussis vaccine bulk at SIIPL involves usage of four strains of *Bordetella pertussis* viz. Strains 134, 509, 6229 and 25525. The Master Seed of Strains 134 and 509 are originally from Rijks Institute, The Netherlands, obtained through National Control Authority, Central Research Institute, Kasauli, Himachal Pradesh, India. The Master Seed of Strains 6229 and 25525 are originally from Lister Institute, England.

Hepatitis B:

Rhein Biotech (Germany) constructed the recombinant Hansenulapolymorpha strain containing the HBsAg surface antigen gene. Rhein Biotech also made the Master Cell Bank (MCB Hansenulapolymorpha K3/8-1 strain ADW, 12/94) and performed all the characterization tests on this bank,

*Haemophilus influenzae* TYPE B:

The source organism for generation of cell substrate is *Haemophilus influenzae* type b, strain 760705. The strain was originally isolated from a 2 year and 2 months old baby boy (born on 14-8-74) in November 1976. Three passages of the strain took place before storage at JO ° C. at the Academic Medical Centre (AMC), University of Amsterdam. This strain was transferred to SIIPL as a part of collaboration between SIIPL and Netherlands Vaccines Institute (NVI, The Netherlands).

IPV:

The strain and source of poliovirus is given below.

Poliovirus Type 1:

Strain: Mahoney

Source: Dr. J. Salk (Pitman & Moore company)

Poliovirus type 2:

Strain: MEF1

Source: Statens Serum Institute, Copenhagen

Poliovirus type 3:

Strain: Saukett

Source: Statens Serum Institute, Copenhagen

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary. While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

Advantages

The present disclosure described herein above has several technical advances and advantages including, but not limited to, the realization of a combination vaccine composition comprising D, T, wP, HBsAg, Hib PRP-TT conjugate and IPV and the method of manufacturing the same. When compared to other combination vaccine composition, the present disclosure provides the following advantages:

1. Fully liquid combination vaccine
2. Improved immunogenicity
3. Reduced Reactogenicity
4. Improved stability at 2-8° C. and room temperature tested over a period of 12 months.
5. A highly purified Diphtheria toxoids (D) & tetanus toxoids (T) produced using semi synthetic medium free of Transmissible Spongiform Encephalopathy (TSE) or Bovine Spongiform Encephalopathy (BSE).
6. Whole-cell *B. pertussis* (wP) antigen comprises *Bordetella pertussis* strains 134, 509, 25525 and 6229 in a ratio of 1:1:0.25:0.25 thereby improving potency and immunogenicity against *B. pertussis.*
7. Improved method of inactivation of whole-cell *B. pertussis* (wP) component using combination of heat and formaldehyde inactivation. The process is devoid of thimerosal and inactivated whole cell pertussis antigen remains non-clumpy and homogeneous thereby leading to reduced reactogenicity and giving better potency for a longer duration.
8. Low Free PRP (less than 7%) in the Total *Haemophilus influenzae* Type b PRP-TT conjugate bulk
9. Improved adsorption profile of Diphtheria toxoid antigen (D), tetanus toxoid (T) antigen and Hepatitis B (HepB) surface antigen adsorbed individually onto aluminium phosphate adjuvant thereby improving potency and immunogenicity.
10. Minimum total alum content ($Al^{3+}$) thereby ensuring reduced reactogenicity.
11. Optimized concentration of 2-phenoxyethanol (2-PE) as preservative.

EXAMPLES

The following examples are included to demonstrate preferred embodiments of the invention. It should be appreciated by those of skill in the art that the compositions and techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Examples 1

TABLE 1

This table gives a brief on the percentage adsorption of individual antigens, Potency and Stability profile of individual antigens in SIIPL Combination vaccine at 2-8° C. over a period of 12 months.

| Test | Limits/ Specification | 0 Day | 6 Months | 12 Months |
|---|---|---|---|---|
| Hepatitis B In-Vivo Potency R.P (95% CL) | NLT 1.0 | Complies | NA | Complies |
| Hib PRP Content (μg/0.5 ml) (Total PRP) | Actual value. | 8.1 μg/0.5 ml | 8.46 μg/0.5 ml | 10.03 |
| Diphtheria component potency (IU/dose) | NLT 30 IU/dose. | 98.5120 IU/dose (69.9650-137.247) | NA | 95.8463 IU/dose |
| Tetanus component potency (IU/dose) | NLT 40 IU/dose | 139.030 IU/dose (88.2850-208.688) | NA | 382.079 IU/dose |
| Pertussis component potency (IU/dose) | NLT 4 IU/dose | 4.6749 IU/dose (2.6492-8.2763) | 4.8410 IU/dose (2.7331-8.6081) | 5.131 |
| Adsorption Hepatitis-B (%) | Actual value. | 89.44 | 82.65 | 75.52 |
| Adsorption: Tetanus Component (%) | Actual value. | 59.0 | 41.0 | NA |
| Adsorption: Diphtheria Component (%) | Actual value. | 79.0 | 72.0 | NA |
| D Antigen (DU/0.5 ml) | Type 1 = 40 DU/0.5 ml, Type 2 = 8 DU/0.5 ml & Type 3 = 32 DU/0.5 ml (=75% of Nominal value is acceptable) | Complies | Complies | Complies |

NA—Not available

TABLE 2

Brief on the Percentage adsorption of individual antigens, Potency and Stability profile of individual antigens in Combination vaccine at 25 ± 2° C. over a period of 12 months.

| Test | Limits/ Specification | 0 Day | 6 Months | 12 Months |
|---|---|---|---|---|
| Hepatitis B In-Vivo Potency R.P (95% CL) | NLT 1.0 | Complies | N.A | Complies |
| Hib PRP Content (μg/0.5 ml) (Total PRP) | Actual value. | 8.6 μg/0.5 ml | 8.20 μg/0.5 ml | NA |
| Diphtheria component potency (IU/dose) | NLT 30 IU/dose. | 98.5120 IU/dose (69.9650-137.247) | N.A | 96.5482 IU/dose (65.9292-137.687) |
| Tetanus component potency (IU/dose) | NLT 40 IU/dose | 139.030 IU/dose (88.2850-208.688) | N.A | N.A |
| Pertussis component potency (IU/dose) | NLT 4 IU/dose | 4.6749 IU/dose (2.6492-8.2763) | 4.5170 IU/dose (2.4894-8.2672) | 3.4899 IU/dose (1.8699*-6.4750) |
| Adsorption Hepatitis-B (%) | Actual value. | 89.44 | 83.92 | 83.00 |
| Adsorption: Tetanus Component (%) | Actual value. | 59.0 | 31.0 | 40.0 |
| Adsorption: Diphtheria Component (%) | Actual value. | 79.0 | 72.0 | 69.0 |
| D Antigen (DU/0.5 mi) | Type 1 = 40 DU/0.5 ml, Type 2 = 8 DU/0.5 ml & Type 3 = 32 DU/0.5 ml (=75% of Nominal value is acceptable) | Complies | Complies | Complies |

NA—Not available

Examples 2

This example gives a brief on the various combination vaccine compositions:

TABLE 3

| Combination Vaccine Composition 1 | | |
|---|---|---|
| Sr. NO. | FORMULATION COMPONENTS | Antigen Unit/0.5 ml Dose |
| 1 | Diphtheria Toxoid (D) | 10-25 Lf |
| 2 | Tetanus toxoid (T) | 02-10 Lf |
| 3 | Inactivated *B. pertussis* antigen (wP) | 12-16 IOU |
| 4 | HBs antigen | 7-15 µg |
| 5 | Hib PRP-TT conjugate antigen | 7-13 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | 2-Phenoxyethanol | 2.5 mg |
| 9 | Sodium Chloride | 4.5 mg |

TABLE 4

| Combination Vaccine Composition 2 | | |
|---|---|---|
| Sr. NO. | FORMULATION COMPONENTS | Antigen Unit/0.5 ml Dose |
| 1 | Diphtheria Toxoid (D) | 10-25 Lf |
| 2 | Tetanus toxoid (T) | 02-10 Lf |
| 3 | Inactivated *B. pertussis* antigen (wP) | 12-16 IOU |
| 4 | HBs antigen | 7-15 µg |
| 5 | Hib PRP-TT conjugate antigen | 7-13 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | Sodium Chloride | 4.5 mg |

TABLE 5

| Combination Vaccine Composition 3 | | |
|---|---|---|
| Sr. NO. | FORMULATION COMPONENTS | Antigen Unit/0.5 ml Dose |
| 1 | Diphtheria Toxoid (D) | 10 Lf |
| 2 | Tetanus toxoid (T) | 02 Lf |
| 3 | Inactivated *B. pertussis* antigen (wP) | 12 IOU |
| 4 | HBs antigen | 8 µg |
| 5 | Hib PRP-TT conjugate antigen | 8 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | 2-Phenoxyethanol | 2.5 mg |
| 9 | Sodium Chloride | 4.5 mg |

TABLE 6

| Combination Vaccine Composition 4 | | |
|---|---|---|
| Sr. NO. | FORMULATION COMPONENTS | Antigen Unit/0.5 ml Dose |
| 1 | Diphtheria Toxoid (D) | 10 Lf |
| 2 | Tetanus toxoid (T) | 02 Lf |
| 3 | Inactivated *B. pertussis* antigen (wP) | 12 IOU |
| 4 | HBs antigen | 8 µg |
| 5 | Hib PRP-TT conjugate antigen | 8 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | Sodium Chloride | 4.5 mg |

TABLE 7

| Combination Vaccine Composition 5 | | |
|---|---|---|
| Sr. NO. | FORMULATION COMPONENTS | Antigen Unit/0.5 ml Dose |
| 1 | Diphtheria Toxoid (D) | 20 Lf |
| 2 | Tetanus toxoid (T) | 04 Lf |
| 3 | Inactivated *B. pertussis* antigen (wP) | 14 IOU |
| 4 | HBs antigen | 15 µg |
| 5 | Hib PRP-TT conjugate antigen | 10 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | 2-Phenoxyethanol | 2.5 mg |
| 9 | Sodium Chloride | 4.5 mg |

TABLE 8

| Combination Vaccine Composition 6 | | |
|---|---|---|
| Sr. NO. | FORMULATION COMPONENTS | Antigen Unit/0.5 ml Dose |
| 1 | Diphtheria Toxoid (D) | 20 Lf |
| 2 | Tetanus toxoid (T) | 04 Lf |
| 3 | Inactivated *B. pertussis* antigen (wP) | 14 IOU |
| 4 | HBs antigen | 15 µg |
| 5 | Hib PRP-TT conjugate antigen | 10 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | Sodium Chloride | 4.5 mg |

TABLE 9

| Combination Vaccine Composition 7 | | |
|---|---|---|
| Sr. NO. | FORMULATION COMPONENTS | Antigen Unit/0.5 ml Dose |
| 1 | Diphtheria Toxoid (D) | 25 Lf |
| 2 | Tetanus toxoid (T) | 10 Lf |
| 3 | Inactivated *B. pertussis* antigen (wP) | 16 IOU |
| 4 | HBs antigen | 15 µg |
| 5 | Hib PRP-TT conjugate antigen | 13 µg of PRP |
| 6 | IPV Type I (D antigen units) | 40 |
| | Type II (D antigen units) | 8 |
| | Type III (D antigen units) | 32 |
| 7 | Adsorbed on Aluminium Phosphate ($Al^{3+}$) | Not more than 0.6 mg |
| 8 | Sodium Chloride | 4.5 mg |

The vaccine may contain traces of glutaraldehyde, formaldehyde, neomycin, streptomycin and polymixin B which are used during the manufacturing process Examples 3

Manufacturing Process of *Haemophilus influenzae* Type b Conjugate Bulk

The broad view of steps of process of manufacturing *Haemophilus influenzae* Type b conjugate bulk is presented with the help of 53 steps of the process which are briefly described below:

Step 1: Inoculum Stage I Shake Flask (S1):

A Working Seed Lot vial is used to inoculate the inoculum stage shake flask, which contains 0.22 μm filtered seed medium. A disposable PETG 125 mL flask with 25 mL working volume is used. This stage is carried out in an incubator shaker with controlled agitation (200±50 rpm) and Temperature (36±2 00). After appropriate bacterial growth is achieved ($OD_{590}$≥1.0), the culture is transferred to next inoculum stage (S2 Stage), which is described in step 2. Gram stain is performed as an in-process control to ensure culture purity (Gram negative cocobacilli).

Step 2: Inoculum Stage II Shake Flask (S2):

S2 inoculum stage consists of 2 L fernbach flasks (S2A and S2B) with 800 mL working volume. S2A flask is used for $OD_{590}$ measurement, till $OD_{590}$ is within acceptance criteria and S2B flask is used for inoculation of S3 stage. Both the flasks are batched with filter-sterilized media, which is identical to the S1 inoculum stage. The S1 stage flask is used to inoculate both the stage II shake flasks. This stage is carried out in an incubator shaker with controlled agitation (200±50 rpm) and Temperature (36±2 00). After appropriate bacterial growth is achieved ($OD_{590}$≥1.0), the culture is transferred to next inoculum stage (S3 Stage), which is described in step 3. Gram stain is performed as an in-process control to ensure culture purity (Gram negative cocobacilli), Step 3: Inoculum Stage III Fermentor:

S3 inoculum stage consists of a 120 L fermenter with a 35 L working volume. The fermenter is batched with a media that is identical to the previous inoculum stages. The S2 stage flask is used to inoculate the Inoculum fermentor. Growth is carried out at temperature (36±2 00), DO (10% set point), agitation (300-600 rpm), aeration (1-5 LPM) and backpressure (0.2 bar) in the inoculum fermenter. After appropriate bacterial growth is achieved ($OD_{590}$≥1.0), the culture is transferred to next production stage (S4 Stage), which is described in step 4. Gram stain is performed as an in-process control to ensure culture purity (Gram negative cocobaccilli).

Step 4: 1200 L Scale Production Fermentation:

The 1200 L production fermenter has a working volume of 800 L. It is batched with basal media components and steam sterilized in-situ. Subsequently, various media supplements are added after passing through a 0.22 μm filter. The fermenter is inoculated with S3 stage culture obtained from step 3. The fermentation is carried under controlled dissolved oxygen (20%-set point), temperature (36±2° C.), pH (7.1-7.4), agitation (40-400 rpm), aeration (50-300 LPM) and backpressure (0.2 bar). Two discrete nutrient spikes are added during the course of the fermentation. The growth is monitored by measuring $OD_{590}$ ($OD_{590}$≥3.5) and fermentation is considered complete after stationary stage is reached, During growth and stationary phase, the polysaccharide product is secreted and accumulates in the culture broth. Gram stain is performed as an in-process control to ensure culture purity (Gram negative cocobacilli).

Step 5: Formalin Treatment:

Bioburden reduction is achieved in this step by using chemical agent (formalin). 0.1% formalin is added and the fermented broth is incubated for NLT 2 hours at 37° C. After the formalin treatment, the vessel is rapidly cooled to <15° C. Formalin addition is validated to achieve bioburden reduction. This is verified by culture plates after the incubation period. The bioburden reduced broth is ready for harvesting as described in step 6.

Step 6: Continuous Centrifugation Harvest:

Continuous centrifugation is employed as a primary harvest step. This step is performed to separate the polysaccharide containing crude broth from the inactivated biomass, A continuous centrifuge is used with the objective of removing>90% of the biomass, as measured by the $OD_{590}$ reduction. The centrifuge is operated at approximately 15000 g and at a liquid flow rate of 200-500 L/h. The centrifuged supernatant is further processed as described in step 7.

Step 7: 50LP Depth Filtration:

The centrifuged supernatant is passed through a 50LP depth filter to remove coarse material such as cell debris. The step allows the product to pass through the filtrate, and is in-line with an additional depth filter, as described in step 8.

Step 8: 90LP Depth Filtration:

The filtrate from the 50LP depth filter is further passed through a 90LP depth filter (nominal 0.22 μm rating) to further remove any insoluble material that may have not been retained by the previous depth filter. This step ensures that filtrate is essentially cell-debris free, and can pass through a 0.22 μm filter robustly. The subsequent filtration step is described in step 9.

Step 9 and 10: 0.22 μm Filtration:

The filtrate from the 90LP depth filter is further passed through a 0.22 μm filter, and the filtrate is collected in hold tank.

Step 11 and 12: 100 kD Concentration and Diafiltration:

This step is carried out to remove media components and small molecular weight impurities. In addition, concentration is performed to reduce the working volume. 100 kD molecular weight cut off is chosen as the molecular weight of the Hib polysaccharide (PRP) is ≥500 kD. The broth is concentrated to approximately 10 fold and subsequently diafiltered for NLT 5 volumes using 0.01 M PBS buffer (pH 7.2). The resulting product in the retentate is referred to as "crude PRP" and is further processed as described in step 13. The concentrated broth is transferred to DSP area through transfer port via 0.22 μm filter to ensure that no bacteria is getting carried over to DSP area.

Step 13: CTAB Precipitation:

CTAB (Cetyl-trimethyl ammonium Bromide) is a cationic detergent, which is used for precipitation of polysaccharide. CTAB consists of a hydrophilic region as well as a hydrophobic part, and precipitates protein, nucleic acid and polysaccharide. Crude PRP obtained from step 12 is precipitated at 1% CTAB concentration and incubated for >2 hours. The CTAB pellet harvesting is described in step 14.

Step 14, 15 and 16: CTAB Pellet Centrifugation, Collection and Storage:

In SEZ-3, FF, CTAB pellet is centrifuged using continuous centrifuge at 15000 rpm. The CTAB pellet is harvested, weighed, aliquoted and stored at ≤−20° C. for further processing. This is the first in-process hold step.

Step 17 and 18: CTAB Paste Thawing and Dissolution:

The frozen CTAB paste is thawed to room temperature. The thawed pellet is dissolved in 5.85% NaCl solution. The dissolution is carried out in a stirred tank and the polysaccharide product is solubilized in the aqueous phase. The tank contains some undissolved material, which comes from precipitated proteins and nucleic acid. This suspension is further processed as described in step 19.

Step 19: Centrifugation:

The material obtained from step 18 is centrifuged at 2-8° C., 5000-6500 rpm for 20-30 minutes to remove the undissolved material. The centrifuged supernatant is collected, and further processed as described in step 20.

Step 20: 72% Ethanol Precipitation:

72% Ethanol is used to precipitate PRP. 96% ethanol is used to generate a final concentration of 72% ethanol with respect to the supernatant obtained in step 19. This precipitation is carried out at 2-8° C. for overnight. The resulting precipitate is harvested as described in step 21.

Step 21 and 22: Centrifugation and Pellet Dissolution:

The 72% ethanol precipitate is collected by centrifugation at 2-8° C., 5000-6500 rpm for 20-30 minutes. The resulting pellet is dissolved in W.F.I. till visual clarity is obtained. Subsequent processing of the solubilized pellet is described in step 23.

Step 23: DOC and 32% Ethanol Precipitation:

To the material obtained from step 22, 6% sodium acetate and 1% sodium Deoxycholate (DOC) is added. 96% ethanol is used to generate a final concentration of 32% ethanol. Both DOC and 32% alcohol drives precipitation of protein impurities, while allowing the polysaccharide to be in the liquid phase. This precipitation is carried out at 2-8° C. for overnight (NLT 8 hrs).

Step 24: Centrifugation:

The material obtained from step 23 is centrifuged at 2-8 00, 5000-6500 rpm for 20-30 minutes to remove the precipitate. The centrifuged supernatant is collected and further processed as described in step 25.

Step 25: Depth and Carbon Filtration:

The supernatant solution obtained in step 24 contains soluble PRP and is subjected to depth filtration followed by carbon filtration to remove nucleic acids and coloring matter. Removal of nucleic acids is monitored by measuring absorbance intermittently at 260 nm ($A_{260}$). After the target $A_{260}$ is reached the solution is filtered through 0.22 μm filter and this filtered solution further processed as described in step 26.

Step 26: 64% Ethanol Precipitation:

The filtered material obtained in step 25 is further precipitated with 96% ethanol at a final concentration of 64% ethanol. This precipitation is carried out at 2-8 00 for overnight. The resulting precipitate is harvested by centrifugation, and further processed as described in step 27.

Step 27: Pellet Collection and Dissolution:

The supernatant is decanted and discarded to collect the pellet. The pellet is dissolved in W.F.I. at room temperature.

Step 28: 300 kD Concentration and Diafiltration:

The dissolved pellet solution is concentrated using 300 kD NMWCO membrane. This is further diafiltered not less than (NLT) 8× using W.F.I. The resultant retentate is processed further as described in step 29.

Step 29 and 30: 0.22 μm Filtration and Purified PRP Storage:

The 300 kD UF retentate is passed through an 0.22 μm filter as a clarification step to minimize bioburden. The resulting purified PRP is aliquoted and stored at ≤−20° C. till further use as described in step 31. Sample of purified PRP is sent for Q.C. analysis.

Step 31: Thawing and Pooling:

Based on conjugate batch size appropriate quantity of native polysaccharide obtained from step 30 is thawed. The pooled material is assayed for PRP content, which is required for further processing as described in step 32.

Step 32: 100 kD Concentration:

The pooled purified polysaccharide is required to be of a minimum concentration (8-12 mg/mL) for further processing. If the pool polysaccharide concentration is below the target, pooled polysaccharide solution is concentrated by using a 100 kD UF NMWCO membrane. Sample is drawn after concentration to ensure that the minimum concentration is reached for subsequent steps (step 33).

Step 33: Alkaline Depolymerization:

The concentrated polysaccharide (equivalent to 74 g/110 g) obtained from step 32 is depolymerized under mild alkaline conditions using carbonate-bicarbonate buffer. After target polysaccharide size is reached, the depolymerized polysaccharide is activated as described in step 34.

Step 34: Polysaccharide Activation:

The depolymerized polysaccharide obtained in step 33 is activated using Cyanogen Bromide. This activation is done under nitrogen environment. Cyanogen bromide is highly toxic chemical and appropriate care is taken while handling this chemical.

Step 35: Linker Attachment:

Freshly prepared adipic acid dihydrazide (ADH) solution is added within 6-10 minutes to the reaction mixture obtained from step 34. The reaction is carried out for NLT 16 hours at 2-10° C. The role of the ADH linker is to provide amine groups in polysaccharide required for conjugation reaction.

Step 36: Concentration and Diafiltration:

The reaction mixture obtained from step 35 is concentrated and diafiltered volume by volume with phosphate buffer saline (PBS) using 10 kD NMWCO UF membrane to remove free ADH. The removal of ADH is monitored on HPLC and diafiltration is continued till free ADH level reaches below 5%. The resulting retentate is further diafiltered with NLT 5X MES-NaCl buffer. This is further concentrated to achieve a concentration of NLT 20 mg/mL. This concentrated processed PRP is kept at 2-8° C. till further use as described in step 37.

Step 37 and 38: 0.22 μm Filtration and Processed PRP Storage:

The retentate from step 36 is passed through a 0.22 μm filter, which serves as a clarification step. This also ensures that bioburden levels are controlled during the process, which is performed in grade C area. The filtered activated polysaccharide is collected, sampled, aliquoted and stored at 2-8° C. till further processing. A sample is drawn from the processed polysaccharide pool for analysis, which includes PRP molecular size (kD), PRP content, and PRP degree of activation. Further processing of the processed PRP is described in step 40.

Step 39: TT 10 kD Concentration and Diafiltration:

The conjugation reaction requires two components viz. processed polysaccharide and the carrier protein (TT). The carrier protein is concentrated and diafiltered with MES-NaCl buffer using 10 kD UF NMWCO membrane. This diafiltered carrier-protein is then further concentrated to NLT 20 mg/mL using the same membrane.

Step 40: Conjugation:

The conjugation reaction requires two components viz. processed polysaccharide and the carrier protein (TT). The activated polysaccharide component is obtained from step 38. The carrier protein is obtained from step 39. The two components are mixed in appropriate quantities in the ratio of PRP: TT=1:1 (w/w) in presence of EDC under stirring. The conjugation reaction is monitored on HPLC and is continued till 85% conversion of protein (based on the free protein conversion to conjugate) is reached.

Step 41: Quenching:

After the conjugation reaction has proceeded to its acceptance criteria for conversion (step 40), the reaction is terminated by quenching. The conjugation reaction is quenched using phosphate EDTA buffer. This conjugation reaction is subsequently processed as described in step 42.

Step 42: 30 SP and 0.22 Micron Filtration:

The conjugate obtained from step 41 is filtered through a 30 SP filter followed by 0.22 μm filtration. This ensures removal of any large aggregates. The filtered conjugate is processed as described in step 43.

Step 43: 300 kD Ultrafiltration and Diafiltration:

The conjugation reaction mixture obtained from step 42 is diafiltered with 0.05% saline using 300 kD UF NMWCO membrane. The diafiltration is performed to remove conjugation reagents and unreacted TT. The resulting retentate is further processed as described in step 44.

Step 44 and 45: 0.22 μm Filtration and Crude Conjugate Storage:

The retentate from step 43 is passed through a 0.22 pm filter, which serves as a clarification step. This also ensures that bioburden levels are controlled during the process, which is performed in grade C area. The filtered crude conjugate is collected, sampled and stored at 2-8° C. till further processing. Further processing of the crude conjugate is described in step 46.

Step 46: Crude Conjugate Dilution:

The crude conjugate from step 45 is diluted with W.F.I. to a target concentration of 4±1 mg/mL, if required and further processed by precipitation steps described in step 47, Step 47: Ammonium Sulphate Precipitation:

The diluted conjugate reaction mixture is further processed to remove free PRP using ammonium sulphate (50% w/v stock solution). The precipitation step is carried out at less than 15° C. under stirring. The precipitation step drives the conjugate in the precipitate, and leaves the free PRP in the supernatant. After addition of ammonium sulphate the resulting suspension is stored at less than 15° C. without stirring for NLT 12 hours.

Step 48: Pellet Collection and Dissolution:

The suspension obtained from step 47 is centrifuged at ~7000 g at 2-8° C. for 40±10 minutes. The supernatant is discarded by decantation and the pellet obtained is dissolved in Tris-saline.

Step 49: 300 kD Diafiltration:

The resulting solution from step 48 is filtered through 30 SP depth filter and diafiltered with 20 mM Tris-Saline using 300 kD NMWCO membrane.

Step 50: GPC Chromatography Purification:

The resulting solution from step 49 is loaded on an approximately 70 L GPC column containing Toyopearl HW-65F hydroxylated methacrylic polymer bead gel for size exclusion chromatography. The use of GPC chromatography for processed conjugate (post-ammonium sulphate) reduces the free PRP levels in the resulting material. The column is eluted with 20 mM Tris 0.9% NaCl, and fractions are collected based on $A_{280}$. Appropriate fractions based on acceptance criteria with respect to free PRP, Ratio and molecular size are pooled, and the pool is further processed, as described in Step 51.

Step 51: 300 kD Diafiltration:

The resulting pooled conjugate eluate from step 50 is diafiltered with 20 mM Tris using 300 kD UF NMWCO membrane. This retentate volume is targeted such that the PRP content in it is approximately 1 mg/mL.

Step 52 and 53: 0.22 μm Filtration:

The bulk conjugate obtained from step 51 is filtered through 0.22 μm filter under grade A environment to ensure sterility. The 0.22 μm filter is integrity tested. A sample from the filtered bulk conjugate is sent to Q.C. for complete analysis. The filtered conjugate is labeled as "Sterile Hib Bulk Conjugate" and stored at 2-8° C. Bulk conjugate will be stored at 2-8° C. for maximum up to 3 months and thereafter if unused, it can be stored at −70° C. for total duration up to 1 year.

Quality characteristics of Hib PRP-TT conjugate antigen obtained were as follow:

PRP content (pg/0.5 ml): 8.1
Ratio (PRP:TT): 0.5
Free PRP (%): 4.8%
PMW (kD): 983
Avg MW (kD): 752

Examples 4

Inactivation Method of Whole Cell Pertussis (wP) Antigen:

Inactivation method optimization is done after performing various experiments which include inactivation at 56° C. for 10 min in presence of formaldehyde, 56° C. for 15 min in presence of formaldehyde, 56° C. for 10 min in presence of hymine, 56° C. for 15 min in presence of hymine and only heating at 56° C. for 30 min. No significant difference in potency is observed with these methods, Out of these methods, 56° C. for 10 min in presence of formaldehyde is selected because pertussis cell mass produced using this method is more homogeneous as compared to other methods mentioned above.

Process of Manufacturing Inactivated wP Antigen Comprises the Following Steps:

a). inactivation at 56° C. for 10-15 minutes in presence of formaldehyde of *Bordetella pertussis* strains 134 b). inactivation at 56° C. for 10-15 minutes in presence of formaldehyde of *Bordetella pertussis* strains 509 c). inactivation at 56° C. for 10-15 minutes in presence of formaldehyde of *Bordetella pertussis* strains 25525 and 6229 c). inactivation at 56° C. for 10-15 minutes in presence of formaldehyde of *Bordetella pertussis* strains 6229 d). subsequently mixing inactivated *Bordetella pertussis* strains 134, 509, 25525 and 6229 in a ratio of 1:1:0.25:0.25.

e). optionally adsorbed onto aluminium based adjuvant.

The process is devoid of thimerosal and inactivated whole cell pertussis antigen remains non-clumpy and homogeneous thereby leading to reduced reactogenicity and giving better potency for a longer duration.

Examples 5: Process of Manufacturing Inactivated Polio Virus (IPV)

Polio Virus May be Grown by Following Method

- CCL81-VERO (Monkey kidney) cell line was used as host cells for the growing of polio viruses i.e. sabin and salk strains.
- After infection of host cells with desired strain of polio virus and incubation of 72 hours, the medium containing the virus and cell debris was pooled and collected in a single container.

The filtrate was subjected to tangential flow filtration with 100 KDa cassette; diafiltered using phosphate buffer and purified using anion exchange chromatography.

Prior to administration to patients, the viruses must be inactivated using appropriate inactivation methods.

Formalin Inactivation Comprising of Following Steps:

a) The purified virus pool was subjected to buffer exchange from Phosphate buffer to Tris buffer in the range of (30 to 50 mM) having pH between 7 to 7.5, b) To the above mixture M-199 medium containing glycine (5 gm/I) was added c) 0.025% formaldehyde was added and subsequently mixed, d) The mixture was subsequently incubated at 37° C. for 5 to 13 days with continuous stirring of virus bulk on magnetic stirrer, e) The post-incubation mixture was subjected to intermediate TFF system (100 KDa, 0.1 $m^2$) on day 7 and final filtration after inactivation f) Subsequently the filtered bulk was stored at 2-8° C., g) Performing D-Ag ELISA for D-Ag unit determination Examples 6

This Example Gives a Brief of the Process of Manufacturing a Combination Vaccine Composition Comprising D, T, wP, HBsAg, Hib PRP-TT Conjugate and IPV:

1. Formulation procedure of component I:
   a). Transfer of aluminum phosphate in the container/vessel
   b). addition of the Diphtheria Toxoid
   c). pH adjustment to 4.5 to 5.5 with Acetic Acid/Sodium Hydroxide
   d). Wait for stabilization
   e). pH adjustment to 5.5 to 6.5 with Sodium Hydroxide/Sodium Carbonate
   f). wait for stabilization
2, Formulation procedure of component II:
   a). Transfer of aluminum phosphate in the container/Vessel
   b). addition of the Tetanus Toxoid
   c). pH adjustment to 4.5 to 5.5 with Acetic Acid/Sodium Hydroxide
   d), Wait for stabilization
   e). pH adjustment to 5.5 to 6.5 with Sodium Hydroxide/Sodium Carbonate
   f). wait for stabilization
3. Formulation procedure of component
   a). Transfer of aluminum phosphate in the container/Vessel
   b). addition of the Hepatitis B surface Antigen
   c). pH adjustment to 4.5 to 5.5 with Acetic Acid/Sodium Hydroxide
   d). Wait for stabilization
   e). pH adjustment to 5.5 to 6.5 with Sodium Hydroxide/Sodium Carbonate
   f). wait for stabilization
4. Mixing of Component f in Component if and agitation at RT.
5. Inactivated wP antigen was added to the above mixture, followed by agitation at RT,
6. Component III was added to the mixture obtained in step 5 at RT
7. Hib PRP conjugate was added to the mixture obtained in step 6 at 6-16° C.
8. IPV antigen was added to the mixture obtained in step 6 at 6-16° C.
9. 2-Phenoxyethanol was added to the mixture obtained in step 7 at 6-16° C.
10. Check the pH, if required adjust the pH 6.0 to 7.0 with—Sodium Hydroxide/Sodium Carbonate
11. NaCl was added to the mixture obtained in step 10, followed by agitation for 3 hours.

Examples 7

Hexavalent Vaccine Toxicity Studies

The following toxicity studies were conducted with DTwP-HepB—IPV-Hib vaccine as per the study plan in compliance with Schedule 'Y' and WHO guidelines on non-clinical evaluation of vaccines and in accordance with the OECD Principles of Good Laboratory Practice.

1. Single Dose Toxicity Study in Sprague Dawley Rats by Subcutaneous Route

A total of 20 male and 20 female rats aged 5-6 weeks at the start of the treatment were randomly divided into four groups. Each group comprised of 5 male and 5 female rats. The ready to use placebo, adjuvant, DTwP-HepB-IPV-Hib single dose vaccine and multi dose vaccine was administered through sub-cutaneous route. Rats were observed for 14 days post dose.

2. Repeated Dose Toxicity Study in Sprague Dawley Rats by Intramuscular Route

A total of 100 male and 100 female rats were randomly allocated to main and recovery groups. The ready to use placebo control, adjuvant control, DTwP-HepB-IPV-Hib single dose vaccine and multi dose vaccine were injected slowly by deep intramuscular injection on Days 1, 29, 57 and 85. Animals in the recovery groups were not treated and observed for 28 Days.

3. Single Dose Toxicity Study in New Zealand White Rabbits by Subcutaneous Route A total of 16 male and 16 female rabbits were randomly divided into four groups. The ready to use placebo, adjuvant, DTwP-HepB-IPV-Hib single dose vaccine and multi dose vaccine was administered through sub-cutaneous route to each animal of the respective group. Rabbits were administered a single subcutaneous dose and observed for 15 days.

4. Repeated Dose Toxicity Study in New Zealand White Rabbits by Intramuscular Route A total of 40 male and 40 female rabbits were randomly allocated to main and recovery groups. The ready-to-use placebo control, adjuvant control and different doses of single and multi-dose DTwP-HepB-IPV-Hib vaccine were injected slowly by deep intramuscular injection on Days 1, 29, 57 and 85. Animals in the recovery groups were not given any treatment and observed for 28 Days.

Based on the results, it was concluded that the single and multi-dose Hexavalent Vaccine [Diphtheria, Tetanus, Pertussis (Whole Cell), Hepatitis-B, Poliomyelitis (inactivated) and *Haemophilus influenzae* type b conjugate Vaccine (Adsorbed)] did not produce any systemic adverse effect in Sprague-Dawley rats and New Zealand White Rabbits when a single human dose (0.5 mL) was administered by sub-cutaneous or intra-muscular route under the test conditions employed. Local injection site inflammatory reactions and findings of immunological response observed in vaccine treated groups are expected and commonly observed in toxicity studies with aluminium adjuvanted vaccines administration. Hence, the test item 'DTwP-HepB-IPV-Hib Vaccine' at the highest dose of 0.5 mL/animal (1 human dose)

is considered "No Observed Adverse Effect Level" (NOAEL), under the test conditions and doses employed.

Example 8

TABLE 10

This table provides comparison of Percentage adsorption of individual antigens, Potency, Free PRP content between SIIPL's Combination Vaccine and Easy Six (Panacea):

| | SIIPL's Combination Vaccine | Panacea Easy-Six ™ Combination Vaccine |
|---|---|---|
| 'D' Ads. (%) | 79.0 | 38.0 |
| 'T' Ads. (%) | 59.0 | 30 |
| HBsAg Ads. (%) | 95.44 | More than 95.0 |
| 'D' Potency (IU/dose) | 98.5120 | More than 40 |
| 'T' Potency (IU/dose) | 139.030 | More than 50 |
| 'HBsAg' In-Vitro Potency (μg/ml) | 35.490 (34.210-36.818) | 23.167 |
| 'HBsAg' In-Vivo Potency (R/P) | 1.07 (0.74-1.57) | 0.71 (0.42-1.13) |
| 'wP' Potency (IU/Dose) | 4.6749 (2.6492-8.2763) | 3.2221 (1.8032-5.7706) |
| HIB (Total PRP) μg/0.5 ml | 8.1 | 13.20 |
| HIB (Free PRP) (%) | 4.8 | 18.45 |
| Free Formaldehyde (% W/V) | 0.0013 | 0.0011 |
| 2-Phenoxyethanol content (mg/0.5 ml) | 2.71 | 3.3 |
| Total Aluminium Content (mg/0.5 ml) | 0.2863 | 0.6034 |
| 'IPV' D antigen (DU/0.5 ml) | Type-I = 39.046<br>Type-II = 7.280<br>Type III = 33.058 | Type-I = 43.504<br>Type-II = 8.056<br>Type III = 39.840 |

D = Diphtheria Toxoid Antigen
T = Tetanus Toxoid Antigen
wP = Whole cell pertussis antigen
HBsAg = Hepatitis B surface Antigen
IPV = Inactivated Polio Virus Antigen
Ads. (%) = Percentage adsorption of Antigen onto aluminium salt ($Al^{3+}$)

We claim:

1. An immunogenic composition, wherein 0.5 ml of the composition comprises
   (i) a diphtheria toxoid, (D) in a range of 10 Lf to 25 Lf, adsorbed onto aluminum salt having percentage adsorption of at least 50%;
   (ii) a tetanus toxoid, (T) in the range of 2 Lf to 10 Lf, adsorbed onto the aluminum salt having percentage adsorption of at least 40%;
   (iii) an inactivated whole cell pertussis antigen (wP) containing inactivated *Bordetella pertussis* strains 134, 509, 25525 and 6229 in a ratio of 1:1:0.25:0.25, in a range of 12 IOU to 16 IOU;
   (iv) a hepatitis B virus surface antigen, (HBsAg) in a range of 7 μg to 15 μg, adsorbed onto the aluminum salt having percentage adsorption of at least 70%;
   (v) a *Haemophilus influenzae* type b (Hib) capsular saccharide conjugated to Tetanus Toxoid as a carrier protein, in a range of 7 μg to 13 μg;
   (vi) an inactivated polio virus antigen, (IPV) containing IPV antigen type 1 in a range of 1-50 DU, Type 2 in a range of 1-20 DU or type 3 in a range of 1-50 DU, respectively;
   (vii) total aluminum content ($Al^{3+}$) as aluminum phosphate adjuvant in a range of 0.1 mg to 0.5 mg;
   (viii) 2-phenoxyethanol as a preservative in a range of 1 mg to 3 mg; and
   (ix) as a dilution medium or buffer including a range of 0.5% to 1.5% NaCl;

wherein the composition is a fully liquid combination vaccine.

2. The immunogenic composition as claimed in claim 1, wherein the IPV antigens are Salk strains selected from a group of Mahoney type 1, MEF Type 2 and Saukett type 3, or Sabin strains selected from a group of Type 1, Type 2 and Type 3.

3. The immunogenic composition as claimed in claim 1, wherein the Hib antigen is a Hib polyribosylribitol phosphate (PRP) polysaccharide conjugated to the carrier protein using a cyanylation conjugation chemistry or reductive amination conjugation chemistry, wherein said cyanylation reagent is selected from Cyanogen Bromide, 1-cyano-4-dimethylaminopyridinium tetrafluoroborate (CDAP)1-cyano-4-pyrrolidinopyridinium tetrafluorborate (CPPT), 1-cyanoimidazole namely (1-CD), 1-cyanobenzotriazole(1-CBT) and 2-cyanopyridazine-3(2H)one (2-CPO).

4. The immunogenic composition as claimed in claim 1, wherein the inactivated whole cell pertussis antigen, the Hib antigen and the inactivated polio virus antigen are not substantially adsorbed on to any adjuvant.

5. The immunogenic composition as claimed in claim 1, wherein the composition comprises D antigen in an amount of about 10 Lf per 0.5 ml to 25 Lf per 0.5 ml; T antigen in an amount of about 2 Lf per 0.5 ml to 10 Lf per 0.5 ml; wP antigen in an amount of about 12 IOU per 0.5 ml to 16 IOU per 0.5 ml; HBsAg in an amount of about 7 μg per 0.5 ml to 15 μg per 0.5 ml; Hib antigen in an amount of about 7 μg per 0.5 ml to 13 μg per 0.5 ml; IPV antigen Salk type 1 in an amount of about 1-50 DU, Salk Type 2 in an amount of about 1-20 DU or Salk type 3 in an amount of about 1-50 DU, respectively, per 0.5 ml; the total aluminum content (Al3+) as aluminum phosphate in the range of 0.1 mg to 0.5 mg per 0.5 ml; 2-Phenoxyethanol in an amount of about 1 mg per 0.5 ml to 3 mg per 0.5 ml; and sodium chloride in an amount of about 0.5% to 1.5%.

6. The immunogenic composition as claimed in claim 1, wherein the composition comprises D antigen in an amount of about 10 Lf per 0.5 ml to 25 Lf per 0.5 ml; T antigen in an amount of about 2 Lf per 0.5 ml to 10 Lf per 0.5 ml; wP antigen in an amount of about 12 IOU per 0.5 ml to 16 IOU per 0.5 ml; HBsAg in an amount of about 7 μg per 0.5 ml to 15 μg per 0.5 ml; Hib antigen in an amount of about 7 μg per 0.5 ml to 13 μg per 0.5 ml; IPV antigen Sabin type 1 in an amount of about 1-50 DU, Sabin Type 2 in an amount of about 1-20 DU or Sabin type 3 in an amount of about 1-50 DU, respectively, per 0.5 ml; the total aluminum content (Al3+) as aluminum phosphate in the range of 0.1 mg to 0.5 mg per 0.5 ml; 2-Phenoxyethanol in an amount of about 1 mg per 0.5 ml to 3 mg per 0.5 ml; and sodium chloride in an amount of about 0.5% to 1.5%.

7. The immunogenic composition as claimed in claim 1, wherein the composition comprises D antigen in an amount of about 10 Lf per 0.5 ml; T antigen in an amount of about 2 Lf per 0.5 ml; wP antigen in an amount of about 12 IOU per 0.5 ml; HBsAg in an amount of about 8 μg per 0.5 ml; Hib antigen in an amount of about 8 μg per 0.5 ml; IPV antigen Salk type 1 in an amount of about 40 DU, Salk Type 2 in an amount of about 8 DU or Salk type 3 in an amount of about 32 DU, respectively, per 0.5 ml; the total aluminum content (Al3+) as aluminum phosphate not more than 0.3 mg to 0.5 mg per 0.5 ml; 2-Phenoxyethanol in an amount of about 2.5 mg per 0.5 ml; and sodium chloride in an amount of about 0.9%.

8. The immunogenic composition as claimed in claim 1, wherein the composition comprises D antigen in an amount of about 20 Lf per 0.5 ml; T antigen in an amount of about 4 Lf per 0.5 ml; wP antigen in an amount of about 14 IOU per 0.5 ml; HBsAg in an amount of about 15 μg per 0.5 ml; Hib antigen in an amount of about 10 μg per 0.5 ml; IPV antigen Salk type 1 in an amount of about 40 DU, Salk Type 2 in an amount of about 8 DU or Salk type 3 in an amount of about 32 DU, respectively, per 0.5 ml; the total aluminum content (Al3+) as aluminum phosphate not more than 0.3 mg per 0.5 ml; 2-Phenoxyethanol in an amount of about 2.5 mg per 0.5 ml; and sodium chloride in an amount of about 0.9%.

9. The immunogenic composition as claimed in claim 1, wherein the composition comprises D antigen in an amount of about 25 Lf per 0.5 ml; T antigen in an amount of about 10 Lf per 0.5 ml; wP antigen in an amount of about 16 IOU per 0.5 ml; HBsAg in an amount of about 15 μg per 0.5 ml; Hib antigen in an amount of about 13 μg per 0.5 ml; IPV antigen Salk type 1 in an amount of about 40 DU, Salk Type 2 in an amount of about 8 DU or Salk type 3 in an amount of about 32 DU, respectively, per 0.5 ml; the total aluminum content (Al3+) as aluminum phosphate not more than 0.3 mg per 0.5 ml; 2-Phenoxyethanol in an amount of about 2.5 mg per 0.5 ml; and sodium chloride in an amount of about 0.9%.

* * * * *

UNITED STATES PATENT AND TRADEMARK OFFICE
CERTIFICATE OF CORRECTION

Page 1 of 1

PATENT NO. : 11,179,453 B2
APPLICATION NO. : 16/631965
DATED : November 23, 2021
INVENTOR(S) : Rakesh Kumar et al.

It is certified that error appears in the above-identified patent and that said Letters Patent is hereby corrected as shown below:

On the Title Page

Item (72) Inventors: please add the following inventors:
--Cyrus Soil Poonawalla, Maharashtra (IN):
Cyrus Adar Poonawalla, Maharashtra (IN)--.

Signed and Sealed this
Eighteenth Day of July, 2023

Katherine Kelly Vidal
*Director of the United States Patent and Trademark Office*